United States Patent
Strobl

(10) Patent No.: US 9,795,590 B2
(45) Date of Patent: Oct. 24, 2017

(54) ANTI-INFLAMMATORY AGENTS AS VIROSTATIC COMPOUNDS

(71) Applicant: Panoptes Pharma GmbH, Vienna (AT)

(72) Inventor: Stefan Strobl, Gauting (DE)

(73) Assignee: PANOPTES PHARMA GMBH, Vienna (AT)

( * ) Notice: Subject to any disclaimer, the term of this patent is extended or adjusted under 35 U.S.C. 154(b) by 0 days.

(21) Appl. No.: 15/302,164

(22) PCT Filed: Apr. 11, 2014

(86) PCT No.: PCT/EP2014/057398
§ 371 (c)(1),
(2) Date: Oct. 5, 2016

(87) PCT Pub. No.: WO2015/154820
PCT Pub. Date: Oct. 15, 2015

(65) Prior Publication Data
US 2017/0027905 A1 Feb. 2, 2017

(51) Int. Cl.
*A61K 31/196* (2006.01)
*A61K 31/341* (2006.01)
*A61K 31/381* (2006.01)
*A61K 31/44* (2006.01)

(52) U.S. Cl.
CPC .......... *A61K 31/381* (2013.01); *A61K 31/196* (2013.01); *A61K 31/341* (2013.01); *A61K 31/44* (2013.01)

(58) Field of Classification Search
None
See application file for complete search history.

(56) References Cited

U.S. PATENT DOCUMENTS

2010/0280081 A1 11/2010 Vitt et al.

FOREIGN PATENT DOCUMENTS

| WO | 03/006425 A2 | 1/2003 |
|---|---|---|
| WO | 2004/056746 A1 | 7/2004 |
| WO | 2004/056747 A1 | 7/2004 |
| WO | 2004/056797 A1 | 7/2004 |
| WO | 2008/077639 A1 | 7/2008 |
| WO | 2009/021696 A1 | 2/2009 |

OTHER PUBLICATIONS

Baumgartner et al, "Dual Binding Mode of a Novel Series of DHODH Inhibitors" Journal of Medicinal Chemistry, 2006, vol. 49, No. 4, pp. 1239-1247.
Chong et al, "Concurrent Antiviral and Immunosuppresive Activites of Leflunomide In Vivo" Am. J. Transplant, 2006, 6(1): 69-75.
Davis et al, "The Immunosuppressive Metabolite of Leflunomide is a Potent Inhibitor of Human Dihydroorotate Dehydrogenase", Biochemistry, 1996, 35(4), 1270-1273.
Kindsmuller et al, "A 49-Kilodalton Isoform of the Adenovirus Type 5 Early Revion 1B 55-Kilodalton Protein Is Sufficient to Support Virus Replication", 2009, J. Virol. 83, 9045-9056.
Leban et al, "Biphenyl-4-ylcarbamoyl thiophene carboxylic acids as potent DHODH inhibitors", Bioorg Med Chem Lett., 2006, 16(2):267-70.
Marschall et al, "In Vitro Evaluation of the Activies of the Novel Anticytomegalovirus Compound AIC246 (letermovir) against Herpesviruses and Other Human Pathogenic Viruses", 2012, Antimicrob. Agents Chemother. 56, 1135-1137.
Marschall et al, "Assessment of drug candidates for broad-spectrum antiviral therapy targeting cellular pyrimidine biosynthesis", Antiviral Research, 2013, vol. 100, No. 3, pp. 640-648.
Meister, Gabriel T. "Antiviral Mechanism(s) of the Experimental Immunosuppressive Agent Leflunomide Against Human Cytomegalovirus and Polyomavirus" dissertation, Ohio State University 2005; 141 pages.
Rechter et al., "Antiviral activity of Arthrospira-derived spirulan-like substances", 2006, Antiviral Res. 72, 197-206.
International Search Report for PCT/EP14/57398 dated Sep. 12, 2014; 4 pages.
Written Opinion for PCT/EP14/57398 dated Sep. 12, 2014; 6 pages.
International Preliminary Report on Patentatiliby for PCT/EP14/57398 dated Oct. 12, 2016; 7 pages.

*Primary Examiner* — Anna Pagonakis
(74) *Attorney, Agent, or Firm* — Loza & Loza, LLP; Michael F. Fedrick

(57) ABSTRACT

The present invention relates to compounds of the general formula (I) and salts and physiologically functional derivatives thereof, for use in the treatment of medical conditions which are caused by an adeno virus, HHV (human herpesvirus), VZV (varicella zoster virus), HSV (herpes simplex virus), EBV (Epstein-Barr virus), vaccinia virus, or BK virus.

(formula I)

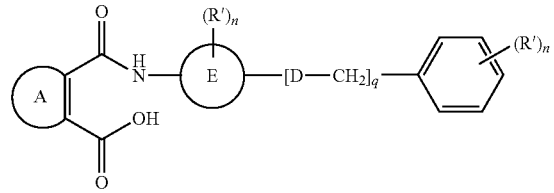

2 Claims, No Drawings

ANTI-INFLAMMATORY AGENTS AS VIROSTATIC COMPOUNDS

CROSS-REFERENCE TO RELATED APPLICATIONS

This application is the U.S. national stage of International Patent Application No. PCT/EP2014/057398, filed on Apr. 11, 2014 and entitled ANTI-INFLAMMATORY AGENTS AS VIROSTATIC COMPOUNDS, the disclosure of which is incorporated herein by reference in its entirety.

FIELD OF THE INVENTION

The present invention relates to compounds of the general formula (I) and salts and physiologically functional derivatives thereof,

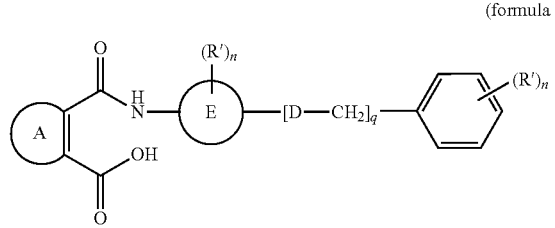

(formula I)

for use in the treatment of medical conditions which are caused by an adeno virus, HHV (human herpesvirus), VZV (varicella zoster virus), HSV (herpes simplex virus), EBV (Epstein-Barr virus), vaccinia virus, or BK virus.

BACKGROUND OF THE INVENTION

Viral infections are usually treated with substances targeting viral proteins, e.g. influenza is treated with M2-membrane protein inhibitors (adamantin and rimantadin) or neuraminidase inhibitors (oseltamivir and zanamivir); HIV is treated with HIV protease inhbitors, reverse transcriptase inhibitors (nucleoside and non-nucleoside analoga), fusion inhibitors (blocking the viral transmembrane protein gp41) or cell entry inhibitors; HCV is treated by a combination of ribavirin and interferone alpha, where ribavirin as a nucleoside analogue inhibits the viral polymerase, and interferone alpha activates the host immune system; HBV is treated with pegylated interferone alpha and/or nucleoside or nucleotide analoga.

However, treatment of these viral diseases is not satisfactory due to the high mutation rate of viruses and the thus resulting lack of efficacy of presently known medications. Moreover, severe side effects caused by interaction with host factors or by incompatibility of treatments for patients who are infected with two or several different viruses occur regularly. In view of the viruses' abilities to quickly adapt to new selection pressures caused by substances targeting viral proteins, new treatment options for viral diseases are urgently required. A new approach to circumvent the selection pressure on viruses and thus avoid the generation of resistances is the targeting of host cell factors vital for the viral replication cycle.

The active metabolite of leflunomide, a DHODH inhibitor with a completely different structure has been discussed and tested lately in several viral infection models as well as in infected patients (Gabriel T. Meister, dissertation Ohio State University 2005; Chong et al. Am. J. Transplant 2006 6(1): 69-75), however, antiviral activity is largely attributed to the inhibition of protein kinases which results in inhibition of phosphorylation of viral proteins. Moreover, administration of uridine in viral plaque assays did not affect the reduction of viral loads in a cytomegalovirus (CMV) model; an inhibitor exerting its activity by the inhibition of DHODH, however, according to the above cited publications would be expected to lose its inhibitory potential when the assay is supplemented with uridine.

The compounds to which this invention relates have been described as DHODH inhibitors before (WO 03/006425, WO 04/056746, WO 04/056797, WO04056747, WO 08/077639, WO 09/021696), and the treatment of diseases caused by viral infections has been mentioned. These compounds are more active DHODH inhibitors when compared to the active metabolite of leflunomide and do not inhibit protein kinases at physiologically relevant levels. Furthermore, it has been shown that the antiviral activity of compounds from this invention can be reversed by addition of uridine (Marshall et al., Antiviral Research 100 (2013) 640-648). Therefore, it is concluded that the antiviral activity of compounds to which this invention relates is based on inhibition of DHODH. In contrast, for the active metabolite of leflunomide antiviral activity is largely attributed to the inhibition of protein kinases.

The pathogenity of viruses heavily relies on host cell machinery for replication, leading to a high need of nucleobase building blocks due to the high replication rate of the viruses. Unexpectedly it has now been found, that the inhibition of DHODH, which leads to an inhibition of the de novo biosyntheses of pyrimidines can be exploited to suppress the replication of certain viruses.

BRIEF SUMMARY OF THE INVENTION

The present invention relates to compounds that surprisingly show virostatic activities. In particular the invention refers to the use of compounds which inhibit dihydroorotate dehydrogenase (DHODH), for the treatment and prevention of viral induced diseases. Diseases or medical conditions according to the present invention are induced by adenovirus, HHV (human herpes viruses), VZV (varicella zoster viruses), HSV (herpes simplex viruses), EBV (Epstein-Barr virus), vaccinia virus, or BK virus, in particular by adenovirus.

Marschall et al. describe a DHODH inhibitor compound which possesses pronounced antiviral activity.

Here we disclose that the use of substances according to formula (I) is particularly advantageous for the treatment of diseases caused by adenoviruses.

Thus, in particular, the subject of the present invention comprises the following aspects:

DETAILED DESCRIPTION OF THE INVENTION

In a first aspect, the invention relates to a compound of formula (I) for use in the treatment or amelioration of a disease or medical condition caused by a viral infection comprising administering to a subject in need thereof an effective amount of a dihydroorotate-dehydrogenase inhibitor of the formula (I)

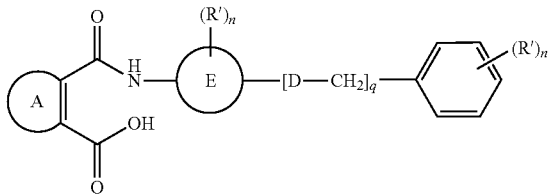

(formula I)

wherein
A is furan, thiophene, phenyl, cyclopentenyl, cyclopentadienyl, pyridyl or dihydrothiophene;
D is O, or S;
R' independently represents halogen, —CO$_2$R", —CONR"R"', —CR"O, —SO$_2$NR", —NR"—CO-haloalkanyl, haloalkenyl, haloalkynyl, —NO$_2$, —NR"—SO$_2$-haloalkanyl, haloalkenyl, haloalkynyl, —NR"—SO$_2$-alkanyl, —NR"—SO$_2$-alkenyl, —NR"—SO$_2$-alkynyl, —SO$_2$-alkanyl, —SO$_2$-alkenyl, —SO$_2$-alkynyl, —NR"—CO-alkanyl, —NR"—CO-alkenyl, —NR"—CO-alkynyl, —CN, alkanyl, alkenyl, alkynyl, cycloalkyl, heterocycloalkyl, aminoalkanyl, aminoalkenyl, aminoalkynyl, alkanylamino, alkenylamino, alkynylamino, alkanyloxy, alkenyloxy, alkynyloxy, -cycloalkyloxy, —OH, —SH, alkanylthio, alkenylthio, alkynylthio, hydroxyalkanyl, hydroxyalkenyl, hydroxyalkynyl, hydroxyalkanylamino, hydroxyalkenylamino, hydroxyalkynylamino, halogen, haloalkanyl, haloalkenyl, haloalkynyl, haloalkanyloxy, haloalkenyloxy, haloalkynyloxy, aryl, aralkyl or heteroaryl;
R" independently represents H, haloalkanyl, haloalkenyl, haloalkynyl, hydroxyalkanyl, hydroxyalkenyl, hydroxyalkynyl, alkanyl, alkenyl, alkynyl, cycloalkyl, heterocycloalkyl, aryl, heteroaryl, aminoalkanyl, aminoalkenyl or aminoalkynyl
R'" independently represents H or alkanyl
E is phenyl or pyridyl, each of which is optionally substituted by one or more substituents R';
n is 0, 1, 2, 3 or 4; and
q is 0 or 1;
or a pharmacologically tolerable salt thereof, or a physiologically functional derivative, which is an ester, phosphate or sulfate modification of a hydroxyl group of a compound of formula I, an ester or amide modification of a carboxylic group of a compound of formula I, or an imine, amide or urea modification of an amino group of a compound of formula I, wherein the viral infection is caused by an adeno virus, HHV (human herpesvirus), VZV (varicella zoster virus), HSV (herpes simplex virus), EBV (Epstein-Barr virus), vaccinia virus, or BK virus.

In another aspect, the invention relates to a compound as described above for use in the treatment or amelioration of a disease or medical condition caused by a viral infection, comprising administering to a subject in need thereof an effective amount of one of the following dihydroorotate-dehydrogenase inhibitors:
3-(2,3,5,6-tetrafluoro-3'-trifluoromethoxy-biphenyl-4-ylcarbamoyl)-thiophene-2-carboxylic acid;
4-(2'-chloro-3,5-difluoro-biphenyl-4-ylcarbamoyl)-2,5-dihydro-thiophene-3-carboxylic acid;
2-[3-chloro-4-(2-chloro-6-fluoro-benzyloxy)-phenylcarbamoyl]-cyclopent-1-enecarboxylic acid;
2-(2,3,5,6-tetrafluoro-3'-trifluoromethoxy-biphenyl-4-ylcarbamoyl)-cyclopent-1-enecarboxylic acid;
2-[4-(2-chloro-6-fluoro-benzyloxy)-3-fluoro-phenylcarbamoyl]-cyclopent-1-enecarboxylic acid;
2-(3-fluoro-3'-methoxy-biphenyl-4-ylcarbamoyl)-cyclopent-1-enecarboxylic acid;
2-(3-biphenyl-4-ylureido)benzoic acid;
2-(2,3,5,6-tetrafluoro-3'-methoxybiphenyl-4-ylcarbamoyl)furan-3-carboxylic acid;
4-(3'-ethoxy-3,5-difluorobiphenyl-4-ylcarbamoyl)thiophene-3-carboxylic acid;
2-(2,3,5,6-tetrafluoro-3'-methoxybiphenyl-4-ylcarbamoyl)cyclopent-1-enecarboxylic acid;
2-(2,3,5,6-tetrafluoro-2'-methoxybiphenyl-4-ylcarbamoyl)cyclopent-1-enecarboxylic acid;
2-(3,5-difluoro-3'-(trifluoromethoxy)biphenyl-4-ylcarbamoyl)cyclopent-1-enecarboxylic acid;
3-hydroxy-2-(2,3,5,6-tetrafluoro-3'-(trifluoromethoxy)biphenyl-4-ylcarbamoyl)cyclopent-1-enecarboxylic acid;
2-(2-chloro-4'-methoxybiphenyl-4-ylcarbamoyl)cyclopent-1-enecarboxylic acid;
4-(3,5-difluoro-3'-(trifluoromethoxy)biphenyl-4-ylcarbamoyl)thiophene-3-carboxylic acid;
5-(4-(2-chloro-6-fluorobenzyloxy)-3-fluorophenylcarbamoyl)cyclopenta-1,4-dienecarboxylic acid;
3-(3,5-difluoro-3'-(trifluoromethoxy)biphenyl-4-ylcarbamoyl)thiophene-2-carboxylic acid;
2-(3-fluoro-3'-methoxybiphenyl-4-ylamino)nicotinic acid;
2-(3,5-difluoro-3'-methoxybiphenyl-4-ylamino)nicotinic acid;
5-cyclopropyl-2-(5-methyl-6-(3-(trifluoromethoxy)phenyl)pyridin-3-ylamino)benzoic acid;
2-[4-(2-chloro-6-fluoro-benzyloxy)-3-fluoro-phenylcarbamoyl]-cyclopent-1-enecarboxylic acid;
2-[3,5-dichloro-4-(2-chloro-6-fluoro-benzyloxy)-phenylcarbamoyl]-cyclopent-1-enecarboxylic acid;
2-(2-chloro-4'-dimethylamino-biphenyl-4-ylcarbamoyl)-cyclopent-1-enecarboxylic acid;
3-(3-fluoro-3'-methoxy-biphenyl-4-ylcarbamoyl)-thiophene-2-carboxylic acid; or
4-(2,3,5,6-Tetrafluoro-3'-trifluoromethoxy-biphenyl-4-ylcarbamoyl)-2,5-dihydro-thiophene-3-carboxylic acid;
or a pharmacologically tolerable salt thereof,
or a physiologically functional derivative thereof, which is an ester, phosphate or sulfate modification of a hydroxyl group of a compound of formula I, an ester or amide modification of a carboxylic group of a compound of formula I, or an imine, amide or urea modification of an amino group of a compound of formula I, wherein the viral infection is caused by an adenovirus, HHV (human herpesvirus), VZV (varicella zoster virus), HSV (herpes simplex virus), EBV (Epstein-Barr virus), vaccinia virus, or BK virus.

In a further aspect, the invention relates to a compound of formula (I) for use as described above, wherein the dihydroorotate-dehydrogenase inhibitor has a half-maximal inhibitory concentration (IC$_{50}$) of 50 nM or less for the inhibition of dihydroorotate-dehydrogenase in an in vitro assay and a half-maximal effective concentration (EC$_{50}$) of 50 μM preferably of 10 μM or less for inhibition of viruses in an in vitro assay.

In a further aspect, the invention relates to a compound of formula (I) for use as described above, wherein the viral infection is caused by an adenovirus In a further aspect, the invention relates to a compound of formula (I) for use as described above, wherein the disease or medical condition is associated with respiratory, gastrointestinal, or ophthalmic symptoms.

In a further aspect, the invention relates to a compound of formula (I) for use as described above, wherein the disease or medical condition is adenoviral conjunctivitis or keratoconjunctivitis.

A further aspect of the present invention is a DHODH inhibitor as described above in a method for the treatment or amelioration of the diseases or medical conditions as detailed herein for the embodiments relating to methods for the treatment or amelioration of said medical conditions.

A further aspect of the present invention is the use of a DHODH inhibitor as described above for the production of a medicament for use in the treatment or amelioration of the diseases or medical conditions as detailed herein for the embodiments relating to methods for the treatment or amelioration of said medical conditions. An example thereof, which is an embodiment of the present invention, is the use of compound 1 for the production of a medicament for use in the treatment or amelioration of a disease or medical conditions caused by a viral infection, more preferably caused by an adenovirus.

A further aspect of the present invention is the use of a DHODH inhibitor as described above for the treatment or amelioration of the diseases or medical conditions as detailed herein for the embodiments relating to methods for the treatment or amelioration of said medical conditions. An example thereof, which is an embodiment of the present invention, is the use of compound 1 for the treatment or amelioration of a disease or medical conditions caused by a viral infection, more preferably caused by an adenovirus.

A further aspect of the present invention is a DHODH inhibitor as described above for the use in the treatment or amelioration of the diseases or medical conditions as detailed herein for the embodiments relating to methods for the treatment or amelioration of said medical conditions. An example thereof, which is an embodiment of the present invention, is compound 1 for the use in the treatment or amelioration of a disease or medical conditions caused by a viral infection, more preferably caused by an adenovirus.

A further aspect of the present invention is a pharmaceutical composition comprising a DHODH inhibitor as described above, and one or more pharmaceutically acceptable excipients for the use in the treatment or amelioration of the diseases or medical conditions as detailed herein for the embodiments relating to methods for the treatment or amelioration of said medical conditions. An example thereof, which is an embodiment of the present invention, is a pharmaceutical composition comprising compound 1 and one or more pharmaceutically acceptable excipients for the use in the treatment or amelioration of a disease or medical conditions caused by a viral infection, more preferably caused by an adenovirus.

An example thereof, which is a preferred embodiment of the present invention, is compound 1 for the use in the treatment or amelioration of a disease or medical conditions caused by a viral infection, more preferably caused by an adenovirus.

A further aspect of the present invention is a pharmaceutical composition comprising a DHODH inhibitor pertaining to the present invention, and one or more pharmaceutically acceptable excipients for the use in the treatment or amelioration of the diseases or medical conditions as detailed herein for the embodiments relating to methods for the treatment or amelioration of said medical conditions. An example thereof, which is an embodiment of the present invention, is a pharmaceutical composition comprising compound 1 and one or more pharmaceutically acceptable excipients for the use in the treatment or amelioration of a disease or medical conditions caused by a viral infection, more preferably caused by an adenovirus.

An alkanyl group, if not stated otherwise, denotes a linear or branched $C_1$-$C_6$-alkanyl, preferably a linear or branched chain of one to five carbon atoms; an alkenyl group, if not stated otherwise, denotes a linear or branched $C_2$-$C_6$-alkenyl group comprising one or more carbon-carbon double bonds and which may further comprise one or more carbon single bonds within its hydrocarbon chain; an alkynyl group, if not stated otherwise, denotes a linear or branched $C_2$-$C_6$-alkinyl group comprising one or more carbon-carbon triple bonds and which may further comprise one or more carbon-carbon double and/or single bonds within its hydrocarbon chain, wherein the alkanyl, alkenyl and alkynyl groups can optionally be substituted by one or more substituents $R^a$, preferably by halogen.

The $C_1$-$C_6$-alkanyl, $C_2$-$C_6$-alkenyl and $C_2$-$C_6$-alkynyl residue may preferably be selected from the group comprising —$CH_3$, —$C_2H_5$, —$CH$=$CH_2$, —C≡CH, —$C_3H_7$, —$CH(CH_3)_2$, —$CH_2$—$CH$=$CH_2$, —$C(CH_3)$=$CH_2$, —$CH$=$CH$—$CH_3$, —C≡C—$CH_3$, —$CH_2$—C≡CH, —$C_4H_9$, —$CH_2$—$CH(CH_3)_2$, —$CH(CH_3)$—$C_2H_5$, —$C(CH_3)_3$, —$C_5H_{11}$, —$C_6H_{13}$, —$C(R^a)_3$, —$C_2(R^a)_5$, —$CH_2$—$C(R^a)_3$, —$C_3(R^a)_7$, —$C_2H_4$—$C(R^a)_3$, —$C_2H_4$—CH=$CH_2$, —CH=CH—$C_2H_5$, —CH=$C(CH_3)_2$, —$CH_2$—CH=CH—$CH_3$, —CH=CH—CH=$CH_2$, —$C_2H_4$—C≡CH, —C≡C—$C_2H_5$, —$CH_2$—C≡C—$CH_3$, —C≡C—CH=$CH_2$, —CH=CH—C≡CH, —C≡C—C≡CH, —$C_2H_4$—$CH(CH_3)_2$, —$CH(CH_3)$—$C_3H_7$, —$CH_2$—$CH(CH_3)$—$C_2H_5$, —$CH(CH_3)$—$CH(CH_3)_2$, —$C(CH_3)_2$—$C_2H_5$, —$CH_2$—$C(CH_3)_3$, —$C_3H_6$—CH=$CH_2$, —CH=CH—$C_3H_7$, —$C_2H_4$—CH=CH—$CH_3$, —$CH_2$—CH=CH—$C_2H_5$, —$CH_2$—CH=CH—CH=$CH_2$, —CH=CH—CH=CH—$CH_3$, —CH=CH—$CH_2$—CH=$CH_2$, —$C(CH_3)$=CH—CH=$CH_2$, —CH=C($CH_3$)—CH=$CH_2$, —CH=CH—$C(CH_3)$=$CH_2$, —$CH_2$—CH=$C(CH_3)_2$, —$C(CH_3)$=$C(CH_3)_2$, —$C_3H_6$—C≡CH, —C≡C—$C_3H_7$, —$C_2H_4$—C≡C—$CH_3$, —$CH_2$—C≡C—$C_2H_5$, —$CH_2$—C≡C—CH=$CH_2$, —$CH_2$—CH=CH—C≡CH, —$CH_2$—C≡C—C≡CH, —C≡C—CH=CH—$CH_3$, —CH=CH—C≡C—$CH_3$, —C≡C—C≡C—$CH_3$, —C≡C—$CH_2$—CH=$CH_2$, —CH=CH—$CH_2$—C≡CH, —C≡C—$CH_2$—C≡CH, —$C(CH_3)$=CH—CH=$CH_2$, —CH=$C(CH_3)$—CH=$CH_2$, —CH=CH—$C(CH_3)$=$CH_2$, —$C(CH_3)$=CH—C≡CH, —CH=$C(CH_3)$—C≡CH, —C≡C—$C(CH_3)$=$CH_2$, —$C_3H_6$—$CH(CH_3)_2$, —$C_2H_4$—$CH(CH_3)$—$C_2H_5$, —$CH(CH_3)$—$C_4H_9$, —$CH_2$—$CH(CH_3)$—$C_3H_7$, —$CH(CH_3)$—$CH_2$—$CH(CH_3)_2$, —CH($CH_3$)—$CH(CH_3)$—$C_2H_5$, —$CH_2$—$CH(CH_3)$—$CH(CH_3)_2$, —$CH_2$—$C(CH_3)_2$—$C_2H_5$, —$C(CH_3)_2$—$C_3H_7$, —$C(CH_3)_2$—$CH(CH_3)_2$, —$C_2H_4$—$C(CH_3)_3$, —$CH(CH_3)$—$C(CH_3)_3$, —$C_4H_8$—CH=$CH_2$, —CH=CH—$C_4H_9$, —$C_3H_6$—CH=CH—$CH_3$, —$CH_2$—CH=CH—$C_3H_7$, —$C_2H_4$—CH=CH—$C_2H_5$, —$CH_2$—$C(CH_3)$=$C(CH_3)_2$, —$C_2H_4$—CH=$C(CH_3)_2$, —$C_4H_8$—C≡CH, —C≡C—$C_4H_9$, —$C_3H_6$—C≡C—$CH_3$, —$CH_2$—C≡C—$C_3H_7$, —$C_2H_4$—C≡C—$C_2H_5$, wherein in all of the above mentioned groups, one or more of the hydrogen atoms can be replaced by a substituent $R^a$, preferably by halogen.

$R^a$ independently represents H, haloalkanyl, haloalkenyl, haloalkynyl, hydroxyalkanyl, hydroxyalkenyl, hydroxyalkynyl, alkanyl, alkenyl, alkynyl, cycloalkyl, heterocycloalkyl, aryl, heteroaryl, aminoalkanyl, aminoalkenyl or aminoalkynyl.

A cycloalkyl group denotes a monocyclic non-aromatic hydrocarbon ring containing three to eight carbon atoms, preferably four to eight carbon atoms, or a bicyclic non-aromatic hydrocarbon ring system containing seven to ten carbon atoms, preferably eight to ten carbon atoms, wherein the cycloalkyl group optionally comprises one or more double bonds, and wherein the cycloalkyl group is optionally substituted by one or more residues $R^a$ as defined above, and wherein in the cycloalkyl group one or two non-consecutive methylene groups may be replaced by a C=O or C=NR$^a$ group; non-limiting examples of the cycloalkyl group are cyclopropanyl, cyclobutanyl, cyclopentanyl, cyclohexanyl, cycloheptanyl and cyclooctanyl, preferably cyclopentanyl, cyclohexanyl or cycloheptanyl, wherein in the afore-mentioned groups optionally one or more of the hydrogen atoms is replaced by a residue R$^a$ as defined above;

A heterocycloalkyl group denotes a monocyclic non-aromatic hydrocarbon ring containing three to eight carbon atoms, preferably four to eight carbon atoms, or a bicyclic non-aromatic hydrocarbon ring system containing seven to ten carbon atoms, preferably eight to ten carbon atoms, wherein in the heterocycloalkyl group one or more of the carbon atoms of the in the hydrocarbon ring or ring system is replaced by a group selected from the group comprising —N(R$^a$)—, —O—, —S—, —S(O)—, —S(O)$_2$—; wherein the heterocycloalkyl group optionally comprises one or more double bonds, and wherein the heterocycloalkyl group is optionally substituted by one or more residues R' as defined above, and wherein in the heterocycloalkyl group one or two methylene groups may be replaced by a C=O or C=NR$^a$ group; non-limiting examples of the heterocycloalkyl group are azepan-1-yl, piperidinyl, in particular piperidin-1-yl and piperidin-4-yl, piperazinyl, in particular N-piperazinyl and 1-alkylpiperazine-4-yl, morpholine-4-yl, tetrahydrofuranyl, tetrahydrothienyl, pyrrolidinyl, tetrahydropyranyl, tetrahydrothiophen, sulfolanyl, sulfolenyl, oxazolinyl, isoxazolinyl, oxazolidinyl, oxazolidinon-yl, wherein in the afore-mentioned groups optionally one or more of the hydrogen atoms is replaced by a residue R$^a$ as defined above.

An alkanyloxy, alkenyloxy or alkynyloxy group denotes an —O-alkanyl, —O-alkenyl or —O-alkynyl group, the alkanyl, alkenyl or alkynyl group being as defined above; the alkanyloxy group is preferably a methoxy, ethoxy, isopropoxy, t-butoxy or pentoxy group.

An alkanylthio, alkenylthio or alkynylthio group denotes an —S-alkanyl, —S-alkenyl or —S-alkynyl group, the alkanyl, alkenyl or alkynyl group being as defined above.

A haloalkanyl, haloalkenyl or haloalkynyl group denotes an alkanyl, alkenyl or alkynyl group which is substituted by one to five halogen atoms, the alkanyl, alkenyl or alkynyl group being as defined above; the haloalkanyl group is preferably a —C(R$^b$)$_3$, —C$_2$(R$^b$)$_5$, —CH$_2$—C(R$^b$)$_3$, —CH$_2$—C(R$^b$)$_3$, —CH(CH$_2$(R$^b$))$_2$, —C$_3$(R$^b$)$_7$ or —C$_2$H$_4$—C(R$^b$)$_3$, wherein instances of R$^b$ may the same or different and each R$^b$ is independently selected from F, Cl, Br or I, preferably F.

A hydroxyalkanyl, hydroxyalkenyl or hydroxyalkynyl, group denotes an HO-alkanyl, HO-alkenyl or HO-alkynyl group, the alkanyl, alkenyl or alkynyl group being as defined above.

A haloalkanyloxy, haloalkenyloxy or haloalkynyloxy group denotes an alkanyloxy, alkenyloxy or alkynyloxy group which is substituted by one to five halogen atoms, the alkanyl, alkenyl or alkynyl group being as defined above; the haloalkanyloxy, haloalkenyloxy or haloalkynyloxy group is preferably a —OC(R$^b$)$_3$, —OC$_2$(R$^b$)$_5$, —OCH$_2$—C(R$^b$)$_3$, —OCH(CH$_2$(R$^b$))$_2$, —OC$_3$(R$^b$)$_7$ or —OC$_2$H$_4$—C(R$^b$)$_3$.

A cycloalkyloxy group denotes an —O-cycloalkyl group; the cycloalkynyloxy group is preferably cyclopropoyx, cyclobutoxy and cyclopentoxy.

A hydroxyalkanylamino, hydroxyalkenylamino or hydroxyalkynylamino group denotes an (HO-alkanyl)$_2$-N—, (HO-alkenyl)$_2$-N— or (HO-alkynyl)$_2$-N-group or HO-alkanyl-NH—, HO-alkenyl-NH— or HO-alkynyl-NH— group, the alkanyl, alkenyl or alkynyl group being as defined above.

An alkanylamino, alkenylamino or alkynylamino group denotes an HN-alkanyl, HN-alkenyl or HN-alkynyl or N-dialkanyl, N-dialkenyl or N-dialkynyl group, the alkanyl, alkenyl or alkynyl group being as defined above.

A halogen group is chlorine, bromine, fluorine or iodine, fluorine being preferred.

An aryl group preferably denotes a mono-, bi-, or tricyclic, preferably monocyclic aromatic hydrocarbon group having six to fifteen carbon atoms, wherein the aryl group is optionally substituted by one or more substituents R', where R' is as defined above; the aryl group is preferably-o-C$_6$H$_4$—R',-m-C$_6$H$_4$—R', -p-C$_6$H$_4$—R', or phenyl, 1-naphthyl, 2-naphthyl, anthracenyl, in particular 1-anthracenyl and 2-anthracenyl group which may optionally be substituted by one or more R', more preferably a phenyl group, -o-C$_6$H$_4$—R',-m-C$_6$H$_4$—R', -p-C$_6$H$_4$—R'.

A heteroaryl group denotes a aromatic 5- or a 6-membered monocyclic aromatic hydrocarbon group wherein at least one of the carbon atoms is replaced by a heteroatom like O, N, S, or a 5- or a 6-membered monocyclic aromatic hydrocarbon group wherein at least one of the carbon atoms is replaced by an N-atom, S, and wherein the aromatic monocyclic 5- or 6-membered cyclic hydrocarbon group is optionally fused to a further monocyclic 5- to 7-membered, preferably 5- or 6-membered, aromatic or nonaromatic hydrocarbon ring, wherein in the further monocyclic aromatic or nonaromatic hydrocarbon ring one or more, preferably one or two carbon atoms may be replaced by a heteroatom like O, N, S; non-limiting examples of heteroaryl groups are thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1-imidazolyl, 2-imidazolyl, 1,2,5-thiadiazol-4-yl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-pyrazinyl, 1-pyrazolyl, 3-pyrazolyl, 4-pyrazolyl, 1H-tetrazol-2-yl, 1H-tetrazol-3-yl, tetrazolyl, indolyl, indolinyl, benzo[b]furanyl, benzo[b]thiophenyl, benzimidazolyl, benzothiazolyl, quinazolinyl, quinoxazolinyl, or preferably quinolinyl, tetrahydroquinolinyl, isoquinolinyl, tetrahydroisoquinolinyl group; the heteroaryl group can optionally be substituted by one or more substituents R$^a$, where R$^a$ is as defined above; the skilled person will acknowledge that in the above definition the replacement of a "carbon atom" by a heteroatom includes any hydrogen atoms bound to said carbon atom.

An aralkyl group denotes an aryl group as defined above which is connected to the molecule of the present invention via an alkanyl, alkenyl or alkynyl bridge, wherein alkanyl, alkenyl or alkynyl is as defined above; preferred aralkyl groups are —CH$_2$—C$_6$H$_5$ (benzyl), —CH$_2$—CH$_2$—C$_6$H$_5$ (phenylethyl), —CH=CH—C$_6$H$_5$, —C≡C—C$_6$H$_5$, -o-CH$_2$—C$_6$H$_4$—R', -m-CH$_2$—C$_6$H$_4$—R', -p-CH$_2$—C$_6$H$_4$—R'; the aralkyl group can optionally be substituted on the aryl and/or alkanyl, alkenyl or alkynyl part by one or more substituents R$^a$, wherein R' is as defined above.

The invention also provides a pharmaceutical composition comprising a compound of formula (I) in free form or in the form of pharmaceutically acceptable salts and physiologically functional derivatives, together with a pharmaceutically acceptable diluent or carrier.

The term "physiologically functional derivative" as used herein refers to compounds which are not pharmaceutically active themselves but which are transformed into their pharmaceutically active form in vivo, i.e. in the subject to which the compound is administered. Examples of physiologically functional derivatives are prodrugs such as those described in the present application.

As used herein, a prodrug is a derivative of a substance that, following administration, is metabolised in vivo, e.g. by hydrolysis or by processing through an enzyme, into an active metabolite. Prodrugs encompass compounds wherein one or more of the chemical groups of said substance are chemically modified, wherein such modifications are for example: ester, phosphate or sulfate derivatives of hydroxyl groups, ester or amide derivatives of carboxylic groups, imine, amide or urea derivatives of amino groups, and the like.

Moreover, the compounds and compositions according to the present invention can be used preferentially when patients are infected with two different viruses or suffer from viral infections and inflammatory or auto-immune diseases.

Specific Embodiments

In certain embodiments A is thiophene or dihydrothiophene.

In certain embodiments A is cyclopentyl or cyclopentadienyl.

In certain embodiments A is phenyl or pyridyl.

In certain embodiments E is phenyl optionally substituted by one or more substituents R', preferably by halogen, more preferably by fluoro.

In certain embodiments D is O.

In certain embodiments q=0.

In certain embodiments R' independently represents halogen, alkanyl, alkenyl, alkynyl, alkanylamino, alkenylamino, alkynylamino, alkanyloxy, alkenyloxy, alkynyloxy, —OH, hydroxyalkanyl, hydroxyalkenyl, hydroxyalkynyl, haloalkanyl, haloalkenyl, haloalkynyl, haloalkanyloxy, haloalkenyloxy, or haloalkynyloxy; preferably R' independently represents H, alkanyl, alkanylamino, alkanyloxy, halogen, haloalkanyl, or haloalkanyloxy.

In further embodiments R' independently represents methyl, dimethylamino, methoxy, ethoxy, F, Cl, or trifluoromethoxy.

In further embodiments R' independently represents F, or trifluoromethoxy.

Exemplary compounds according to this invention include any one selected from Table 1 and the salts thereof, specifically preferred compound 1.

The skilled person will appreciate that the present invention does not encompass compounds comprising chemically unstable entities, such as for instance ozone groups or groups containing pentavalent carbon atoms or trivalent oxygen atoms, and the like. Accordingly, combinations or variations of the chemical groups and moieties described herein which lead to such chemically unstable entities are excluded.

The cycloalkyl, heterocycloalkyl, aryl, heteroaryl, alkanyl, alkenyl, alkynyl groups and groups derived from alkanyl, alkenyl or alkynyl (such as for instance alkanyloxy) as defined herein, irrespective of a possible substitution with one or more residues R', may be a terminal group on a side chain branch of the compounds of the present invention or may be placed in within a side chain branch of the compounds of the present invention. Accordingly, in the context of the present invention, the above mentioned terms encompass cycloalkylene, heterocycloalkylene, arylene, heteroarylene, alkanylene, alkenylene, alkynylene groups and groups derived from alkanylene, alkenylene or alkynylene.

In the compounds of the present invention, the residues R' and R'' preferably may not be substituted by a group comprising a second or otherwise further residue selected from R' and/or R''. This is to be understood such that compounds comprising oligomeric or polymeric side chains comprising multiple R' and/or R'' units are preferably not encompassed by the present invention.

It is to be understood that the specific embodiments described above may be combined in any suitable and chemically reasonable fashion to furnish further specific embodiments.

Due to their favourable pharmacokinetic properties, the compounds of the present invention are suited for oral treatment regimen wherein the medicament comprising the compound according to the present invention is administered once daily.

In one embodiment, the compounds of the present invention are for the treatment or amelioration of a disease or medical condition caused by Adeno virus.

Preferably, the compounds according to the invention have a half-maximal inhibitory concentration ($IC_{50}$) of 1 µM or less, more preferably 200 nM or less, and even more preferably 20 nM or less for the inhibition of dihydroorotate-dehydrogenase in an in vitro assay and a half-maximal effective concentration ($EC_{50}$) of 10 µM or less, preferably 1 µM or less and even more preferably 200 nM or less for inhibition of viruses in an in vitro assay.

Preferably, the compounds according to the invention have a solubility in water of 5 µg/mL or greater, preferably 10 µg/mL or greater and/or an absolute oral availability (F) of 10% or greater, more preferably 30% or greater.

Preferably, the compounds according to the invention exhibit a high solubility in polar, protic solvents, such as in water (solubility (>10 µg/mL $H_2O$) and/or their oral availability (F) is >30%. Moreover, preferably the compounds of the present invention are chemically stable and the manufacture thereof is inexpensive and straight forward. Accordingly, manufacture of the compounds of the present invention is cost effective.

Due to the mode of action of the compounds of the present invention, which involves the interaction with a host-cell based target, the generation of resistant viral strains is unlikely.

TABLE 1

| # | Structure | IUPAC name |
|---|-----------|------------|
| 1 | 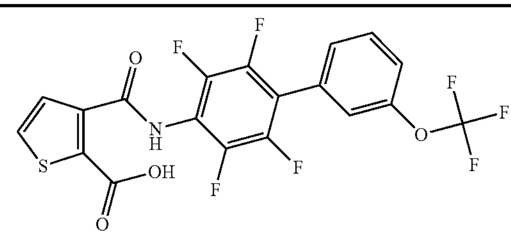 | 3-(2,3,5,6-tetrafluoro-3'-trifluoromethoxy-biphenyl-4-ylcarbamoyl)-thiophene-2-carboxylic acid |

TABLE 1-continued

| # | Structure | IUPAC name |
|---|---|---|
| 2 | 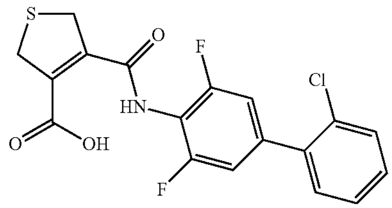 [SMILES: O=C(O)C1=C(C(=O)Nc2c(F)cc(-c3ccccc3Cl)cc2F)CSC1] | 4-(2'-chloro-3,5-difluoro-biphenyl-4-ylcarbamoyl)-2,5-dihydro-thiophene-3-carboxylic acid |
| 3 | 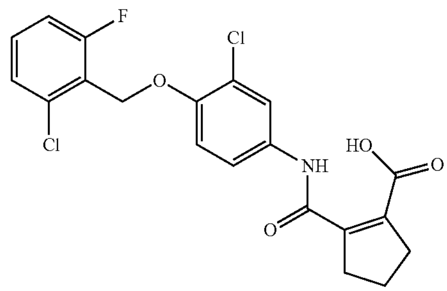 [SMILES: O=C(O)C1=C(C(=O)Nc2ccc(OCc3c(F)cccc3Cl)c(Cl)c2)CCC1] | 2-[3-chloro-4-(2-chloro-6-fluoro-benzyloxy)-phenylcarbamoyl]-cyclopent-1-enecarboxylic acid |
| 4 | 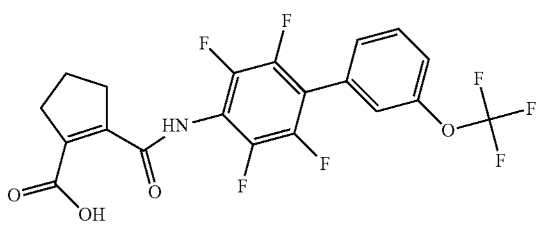 [SMILES: O=C(O)C1=C(C(=O)Nc2c(F)c(F)c(-c3cccc(OC(F)(F)F)c3)c(F)c2F)CCC1] | 2-(2,3,5,6-tetrafluoro-3'-trifluoromethoxy-biphenyl-4-ylcarbamoyl)-cyclopent-1-enecarboxylic acid |
| 5 | 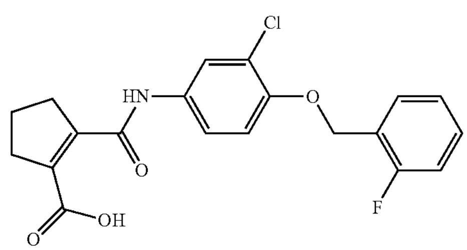 [SMILES: O=C(O)C1=C(C(=O)Nc2ccc(OCc3ccccc3F)c(Cl)c2)CCC1] | 2-[4-(2-chloro-6-fluoro-benzyloxy)-3-fluoro-phenylcarbamoyl]-cyclopent-1-enecarboxylic acid |
| 6 | 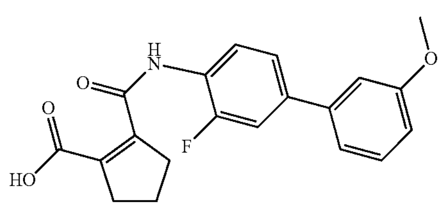 [SMILES: COc1cccc(-c2ccc(NC(=O)C3=C(C(=O)O)CCC3)c(F)c2)c1] | 2-(3-fluoro-3'-methoxy-biphenyl-4-ylcarbamoyl)-cyclopent-1-enecarboxylic acid |
| 7 | 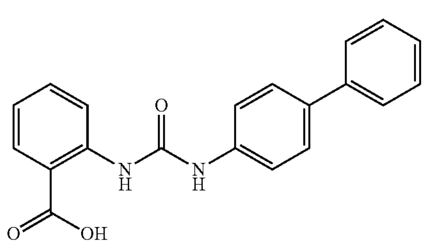 [SMILES: O=C(Nc1ccc(-c2ccccc2)cc1)Nc1ccccc1C(=O)O] | 2-(3-biphenyl-4-ylureido)benzoic acid |
| 8 | 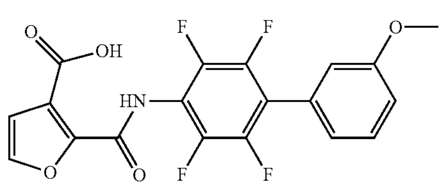 [SMILES: COc1cccc(-c2c(F)c(F)c(NC(=O)c3occc3C(=O)O)c(F)c2F)c1] | 2-(2,3,5,6-tetrafluoro-3'-methoxybiphenyl-4-ylcarbamoyl)furan-3-carboxylic acid |

TABLE 1-continued

| # | Structure | IUPAC name |
|---|---|---|
| 9 | 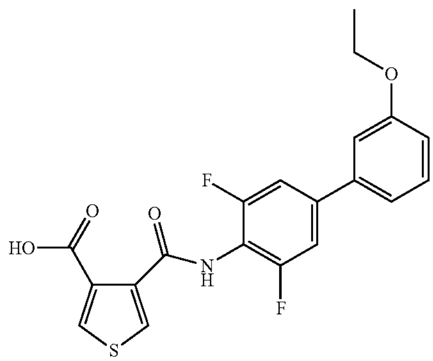 [SMILES: CCOc1cccc(-c2cc(F)c(NC(=O)c3cscc3C(=O)O)c(F)c2)c1] | 4-(3'-ethoxy-3,5-difluorobiphenyl-4-ylcarbamoyl)thiophene-3-carboxylic acid |
| 10 | 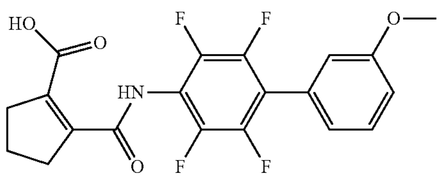 [SMILES: COc1cccc(-c2c(F)c(F)c(NC(=O)C3=C(C(=O)O)CCC3)c(F)c2F)c1] | 2-(2,3,5,6-tetrafluoro-3'-methoxybiphenyl-4-ylcarbamoyl)cyclopent-1-enecarboxylic acid |
| 11 | 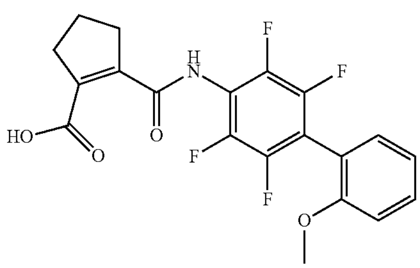 [SMILES: COc1ccccc1-c1c(F)c(F)c(NC(=O)C2=C(C(=O)O)CCC2)c(F)c1F] | 2-(2,3,5,6-tetrafluoro-2'-methoxybiphenyl-4-ylcarbamoyl)cyclopent-1-enecarboxylic acid |
| 12 | 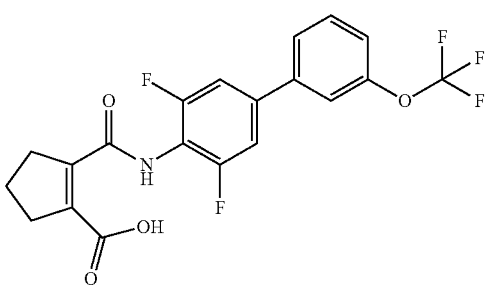 [SMILES: O=C(O)C1=C(C(=O)Nc2c(F)cc(-c3cccc(OC(F)(F)F)c3)cc2F)CCC1] | 2-(3,5-difluoro-3'-(trifluoromethoxy)biphenyl-4-ylcarbamoyl)cyclopent-1-enecarboxylic acid |
| 13 | 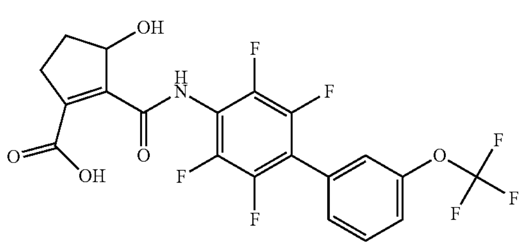 [SMILES: O=C(O)C1=C(C(=O)Nc2c(F)c(F)c(-c3cccc(OC(F)(F)F)c3)c(F)c2F)C(O)CC1] | 3-hydroxy-2-(2,3,5,6-tetrafluoro-3'-(trifluoromethoxy)biphenyl-4-ylcarbamoyl)cyclopent-1-enecarboxylic acid |

TABLE 1-continued

| # | Structure | IUPAC name |
|---|---|---|
| 14 | 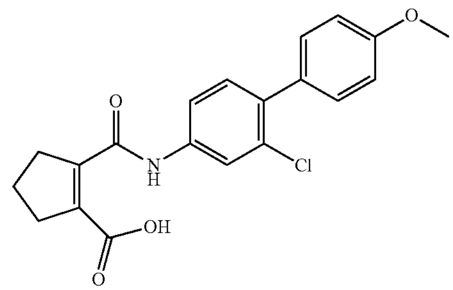 [SMILES: COc1ccc(-c2ccc(NC(=O)C3=C(C(=O)O)CCC3)cc2Cl)cc1] | 2-(2-chloro-4'-methoxybiphenyl-4-ylcarbamoyl)cyclopent-1-enecarboxylic acid |
| 15 | 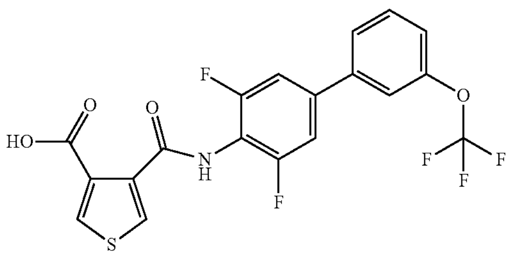 [SMILES: O=C(O)c1cscc1C(=O)Nc1c(F)cc(-c2cccc(OC(F)(F)F)c2)cc1F] | 4-(3,5-difluoro-3'-(trifluoromethoxy)biphenyl-4-ylcarbamoyl)thiophene-3-carboxylic acid |
| 16 | 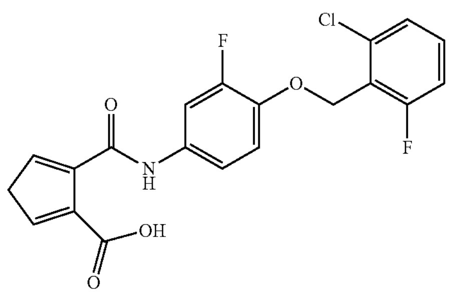 [SMILES: O=C(O)C1=CCC=C1C(=O)Nc1ccc(OCc2c(F)cccc2Cl)c(F)c1] | 5-(4-(2-chloro-6-fluorobenzyloxy)-3-fluorophenylcarbamoyl)cyclopenta-1,4-dienecarboxylic acid |
| 17 | 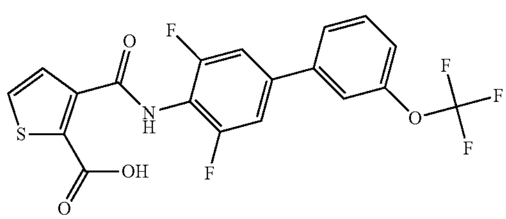 [SMILES: O=C(Nc1c(F)cc(-c2cccc(OC(F)(F)F)c2)cc1F)c1ccsc1C(=O)O] | 3-(3,5-difluoro-3'-(trifluoromethoxy)biphenyl-4-ylcarbamoyl)thiophene-2-carboxylic acid |
| 18 | 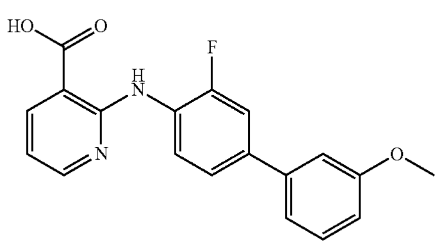 [SMILES: COc1cccc(-c2ccc(Nc3ncccc3C(=O)O)c(F)c2)c1] | 2-(3-fluoro-3'-methoxybiphenyl-4-ylamino)nicotinic acid |
| 19 | 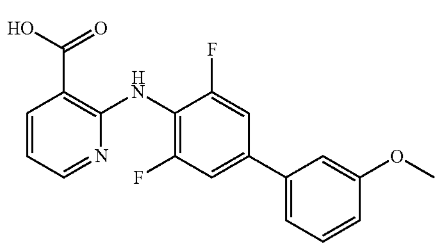 [SMILES: COc1cccc(-c2cc(F)c(Nc3ncccc3C(=O)O)c(F)c2)c1] | 2-(3,5-difluoro-3'-methoxybiphenyl-4-ylamino)nicotinic acid |

TABLE 1-continued

| # | Structure | IUPAC name |
|---|---|---|
| 20 | 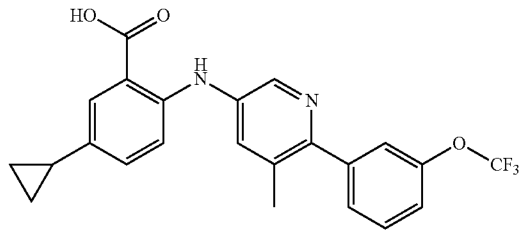 [SMILES: Cc1cc(Nc2ccc(C3CC3)cc2C(=O)O)cnc1-c1cccc(OC(F)(F)F)c1] | 5-cyclopropyl-2-(5-methyl-6-(3-(trifluoromethoxy)phenyl)pyridin-3-ylamino)benzoic acid |
| 21 | 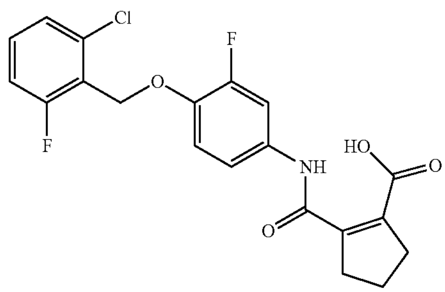 [SMILES: O=C(O)C1=C(C(=O)Nc2ccc(OCc3c(F)cccc3Cl)c(F)c2)CCC1] | 2-[4-(2-Chloro-6-fluoro-benzyloxy)-3-fluoro-phenylcarbamoyl]-cyclopent-1-enecarboxylic acid |
| 22 | 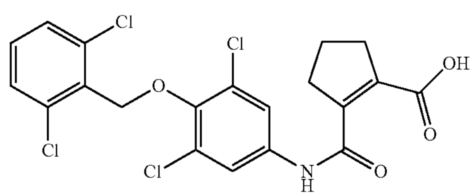 [SMILES: O=C(O)C1=C(C(=O)Nc2cc(Cl)c(OCc3c(Cl)cccc3Cl)c(Cl)c2)CCC1] | 2-[3,5-Dichloro-4-(2-chloro-6-fluoro-benzyloxy)-phenylcarbamoyl]-cyclopent-1-enecarboxylic acid |
| 23 | 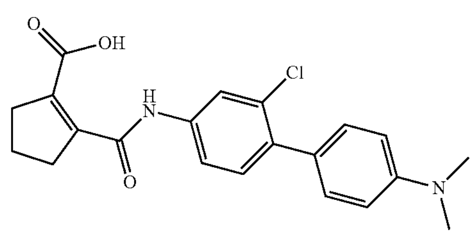 [SMILES: CN(C)c1ccc(-c2ccc(NC(=O)C3=C(C(=O)O)CCC3)cc2Cl)cc1] | 2-(2-Chloro-4'-dimethylamino-biphenyl-4-ylcarbamoyl)-cyclopent-1-enecarboxylic acid |
| 24 | 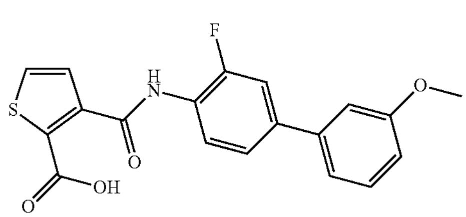 [SMILES: COc1cccc(-c2ccc(NC(=O)c3ccsc3C(=O)O)c(F)c2)c1] | 3-(3-Fluoro-3'-methoxy-biphenyl-4-ylcarbamoyl)-thiophene-2-carboxylic acid |
| 25 | 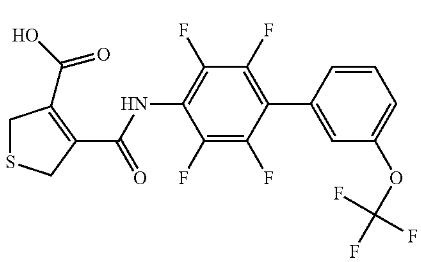 [SMILES: O=C(O)C1=C(C(=O)Nc2c(F)c(F)c(-c3cccc(OC(F)(F)F)c3)c(F)c2F)CSC1] | 4-(2,3,5,6-Tetrafluoro-3'-trifluoromethoxy-biphenyl-4-ylcarbamoyl)-2,5-dihydro-thiophene-3-carboxylic acid |

Examples

1. Determination of Pharmacological Parameters of Compound 1

Pharmacological parameters of compound 1 (Table 2) were determined by standard procedures, i.e. DHODH and kinase activity assays were performed according to Davis et al., (1996. The immunosuppressive metabolite of leflunomide is a potent inhibitor of human dihydroorotate dehydrogenase. Biochemistry 35, 1270-1273) and www.DiscoverX.com standard protocols, respectively;

TABLE 2

| Inhibitory activity in vitro | ($IC_{50}$) |
|---|---|
| DHODH (human) | 1.5 ± 0.2 nM |
| DHODH (mouse) | 3.2 ± 0.8 nM |
| PI3K-α/-β/-γ/-δ | >1 µM |
| AKT-1/-2/-3 | >15 µM |
| JAK-1/-2/-3 | >10 µM |

2. Inhibition of Human and Murine DHODH

Analysis of in vitro enzymatic activity was performed by the use of purified human DHODH in an established assay as described before (Davis et al., Biochemistry. 1996 Jan. 30; 35(4):1270-3; Leban et al., Bioorg Med Chem Lett. 2006 Jan. 15; 16(2):267-70). Putative inhibitory compounds were directly applied to the reaction in a concentration range between 100 µM and 10 µM.

A strong and selective inhibition of human and murine DHODH could be demonstrated in vitro with $IC_{50}$ values of 1.5±0.2 nM and 3.2±0.8 nM, respectively (Table 2). In a comparative setting, the nucleoside analogue GCV (used as anti-cytomegaloviral reference drug) did not exert any inhibition on DHODH in vitro. No effects onto human DHODH were measured up to high concentrations of GCV (duplicate testings), i.e. DHODH exerted 100% activity even at 10 µM. This finding underlined the specificity of compound 1 and confirmed its strong and concentration-dependent anti-DHODH activity. Other enzymes, not related to DHODH, such as a series of protein kinases including PI3K, AKT and JAK (three to four isoforms each), were not inhibited by compound 1 (Table 2).

3. Antiviral Assay in Cell Culture

Antiviral assays were performed as described in the literature (Marschall, M. et al., 2000. Antimicrob. Agents Chemother. 44, 1588-1597; Marschall M. et al., 2012. Antimicrob. Agents Chemother. 56, 1135-1137; Kindsmüller et al., 2009. J. Virol. 83, 9045-9056; Rechter et al., 2006. Antiviral Res. 72, 197-206).

Human adenovirus type 2 (HAdV-2) showed high level of sensitivity ($IC_{50}$ 0.56±0.02 µM; Table 3) as measured in a standard plaque reduction assay. This result was confirmed and substantiated by performing a previously established virus yield assay (Kindsmüller et al., 2009. J. Virol. 83, 9045-9056) with a series of HAdVs spanning virus species A to E (one to three types each, including clinical isolates B03k and E04k).

A549 cells were infected at MOI 20 and continuously treated with the given concentrations of compound 1. Virus-containing supernatants were transferred to uninfected cells at 4 d[1], 6 d[2] or 2 d[3] post-infection, respectively, and used for quantitation of infectious virus. Percentages of virus-positive cells per total cells were determined on the basis of indirect immunofluorescence staining (monoclonal anti-adenovirus hexon protein antibody; Abcam B025-AD51/ab7428) by microscopic countings: n=4 for C02, C05, D19, D37; n=3 for B03k, E04k; n=1 for A31, B03, D08, E04.

This selection of HAdVs represented the natural variety of adenovirus-induced pathogenic infections, i.e. association with respiratory, gastrointestinal, ophthalmic or other types of symptoms. Importantly, all HAdVs were subject to inhibition at a drug concentration of 1.11 µM, in an efficacy range between 71% and 100% (Table 4). Highest sensitivity was seen for virus species A, C and D, lower sensitivity for B and E.

TABLE 3

Analysis of the antiviral activity of compound 1 against HAdV-2

| $IC_{50}$ | 0.56 ± 0.00 µM (n = 8) |
|---|---|
| Cytotoxicity (1-10 µM) | None |

TABLE 4

| | compound 1 | | |
|---|---|---|---|
| HAdV | 0 µM | 0.37 µM | 1.11 µM |
| A31[1] | 100 | 72 | 3 |
| B03[2] | 100 | 127 | 29 |
| B03k[2] | 100 | 70 | 11 |
| C02[3] | 100 | 100 | 9 |
| C05[3] | 100 | 82 | 6 |
| D08[1] | 100 | 6 | 0 |
| D19[1] | 100 | 81 | 4 |
| D37[2] | 100 | 96 | 3 |
| E04[2] | 100 | 128 | 23 |
| E04k[2] | 100 | 115 | 9 |

TABLE 5

Comparative analysis of the antiviral activity of Compound 1*

| Virus | HHV-6 | VZV | HSV-1 | HSV-2 |
|---|---|---|---|---|
| $IC_{50}$ [µM][†] | 1.55 ± 0.31 (n = 8) | 3.55 ± 0.26 (n = 4) | >10 (n = 4) | >10 (n = 4) |
| Cytotoxicity [1-10 µM][‡] | none | none | none | none |

Comparative analysis of the antiviral activity of Compound 1*

| Virus | EBV | Vaccina | HadV-2 |
|---|---|---|---|
| $IC_{50}$ [µM][†] | >10 (n = 4) | 9.85 ± 6.61 (n = 4) | 0.56+ ± 0 (n = 8) |
| Cytotoxicity [1-10 µM][‡] | none | none | none |

*Viruses and cells used: HHV-6, human herpesvirus type 6A, strain U1102, J-JHAN; VZV, varicella zoster virus, strain Oka, primary human fibroblasts; HSV-1 and HSV-2, herpes simplex virus types 1 and 2, strain 166v VP22-GFP and isolate 01-6332, respectively, Vero; EBV, Epstein-Barr virus, strain B95-8, 293T (T81GFP); vaccine virus, strain IHD-5, primary human fibroblasts; HAdV-2 human adenovirus type 2, A549.
[†]The 50% inhibitory concentrations of virus replication were determined by GFP-based reporter assay (HCMV, HSV-1) or plaque reduction assay, respectively. Mean values and standard deviations dereived from n-fold measurements are given.
[‡]Drug-induced cytotoxicity was determined by microscopic evaluation performed at two separate time points during the course of the experiment.

The invention claimed is:

1. A method of treating adenoviral conjunctivitis, comprising administering to a subject in need thereof an effective amount of the compound 3-(2,3,5,6-tetrafluoro-3'-trifluoromethoxy-biphenyl-4-ylcarbamoyl)-thiophene-2-carboxylic acid or a pharmaceutically acceptable salt thereof.

2. The method of claim 1, wherein the compound has a half-maximal inhibitory concentration (IC50) of 50 nM or less for the inhibition of dihydroorotate-dehydrogenase in an in vitro assay and a half-maximal effective concentration (EC50) of 50 μM or less for inhibition of adenoviruses in an in vitro assay.

* * * * *